US010779802B2

(12) United States Patent
Tholen et al.

(10) Patent No.: US 10,779,802 B2
(45) Date of Patent: Sep. 22, 2020

(54) SYSTEM AND METHOD FOR DETERMINING THE FERTILITY PHASE OF A FEMALE

(71) Applicant: AVA AG, Zürich (CH)

(72) Inventors: Philipp Tholen, Zürich (CH); Pascal Koenig, Zürich (CH); Peter Stein, Zürich (CH)

(73) Assignee: AVA AG, Zürich (CH)

( * ) Notice: Subject to any disclaimer, the term of this patent is extended or adjusted under 35 U.S.C. 154(b) by 298 days.

(21) Appl. No.: 15/550,976

(22) PCT Filed: Jan. 28, 2016

(86) PCT No.: PCT/EP2016/051819
§ 371 (c)(1),
(2) Date: Aug. 14, 2017

(87) PCT Pub. No.: WO2016/131630
PCT Pub. Date: Aug. 25, 2016

(65) Prior Publication Data
US 2018/0035982 A1 Feb. 8, 2018

(30) Foreign Application Priority Data
Feb. 16, 2015 (CH) .......................................... 208/15

(51) Int. Cl.
*A61B 5/1455* (2006.01)
*A61B 10/00* (2006.01)

(52) U.S. Cl.
CPC .. *A61B 10/0012* (2013.01); *A61B 2010/0016* (2013.01); *A61B 2010/0019* (2013.01); *A61B 2010/0029* (2013.01)

(58) Field of Classification Search
None
See application file for complete search history.

(56) References Cited

U.S. PATENT DOCUMENTS

| 2002/0156394 A1 | 10/2002 | Mehrotra et al. |
| 2013/0072765 A1 | 3/2013 | Kahn et al. |
| 2014/0246500 A1 | 9/2014 | Proud et al. |

FOREIGN PATENT DOCUMENTS

| CN | 104224239 A | 12/2014 |
| EP | 132119 A2 | 1/1985 |

(Continued)

OTHER PUBLICATIONS

International Search Report and Written Opinion of the International Searching Authority for International Application No. PCT/EP2016/051819, dated Apr. 14, 2016.

(Continued)

*Primary Examiner* — Eric F Winakur
*Assistant Examiner* — Marjan Fardanesh
(74) *Attorney, Agent, or Firm* — Knobbe, Martens, Olson & Bear, LLP (57) ABSTRACT

An electronic system for determining a fertility phase of a female human comprises a wearable device (1) that includes a first sensor system (101), configured to determine heart rate and heart rate variability of the female human, and a second sensor system (102), configured to determine acceleration of the female human. The electronic system further comprises a processor (13, 30), configured to detect during menstrual cycles sleep phases with resting pulse, using the heart rate variability and the acceleration, to determine a change in the resting pulse during a menstrual cycle using the heart rate, and to determine the fertility phase using a time of the change in the resting pulse. The processor for determining the fertility phase is implemented in the wearable device (1), in a mobile communication device (4), and/or in a cloud-based computer system (3).

18 Claims, 7 Drawing Sheets

(56) References Cited

FOREIGN PATENT DOCUMENTS

| | | |
|---|---|---|
| GB | 2143332 A | 2/1985 |
| WO | WO 2013/171799 A1 | 11/2013 |
| WO | WO 2014/207484 A1 | 12/2014 |
| WO | WO-2015150434 A1 * 10/2015 | ......... A61B 10/0012 |

* cited by examiner

SYSTEM AND METHOD FOR DETERMINING THE FERTILITY PHASE OF A FEMALE

FIELD OF THE INVENTION

The present invention relates to an electronic system and a method for determining a fertility phase of a female human. Specifically, the present invention relates to an electronic system and a method for determining a fertility phase of a female human using a wearable device with sensor systems for measuring physiological parameters.

BACKGROUND OF THE INVENTION

Since the introduction of the contraceptive pill in 1960, decades have passed without major developments in the birth control market. Within the last years so called fertility apps for mobile devices were becoming attractive for an increasing number of women. These applications use the calendar method for determining fertile time periods. Nevertheless, most non-hormonal birth control tools, such as these apps or the well known temperature method, are found cumbersome and unreliable by many women. Generally, by relying on more than one physiological parameter the reliability can be increased significantly for determining the fertility phase of a female in connection with non-hormonal birth control. For example, the so called symptothermal method uses a combined analysis of cervical mucus and temperature measurements for determining the fertile and infertile days of a woman. While this yields a better reliability, it is typically found complicated and very cumbersome by women.

WO 97/22298 describes an apparatus with a microprocessor that processes data from wrist worn sensors measuring eccrine sweat to observe the pattern in pH change during the menstrual cycle for determining the fertility status of a female.

CN 203314947U describes a multifunctional watch that comprises a microprocessor and a temperature sensor for monitoring the menstrual cycle of a female.

US 2004/081024 describes another wristwatch that comprises a temperature sensor and a computing device for predicting the ovulation phase.

US 2002/0156394 describes an apparatus which is inserted into the vagina of cattle for detecting estrus.

US 2014/246500 mentions that ovulation can be detected with wrist based collected data. US 2014/246500 does neither describe how to process the collected data, nor make it possible to predict ovulation and to determine in advance the fertile phase which would be valuable for women who want to become pregnant.

SUMMARY OF THE INVENTION

It is an object of this invention to provide an electronic system and a method for determining the fertility phase of a female human, which system and method do not have at least some of the disadvantages of the prior art. In particular, it is an object of the present invention to provide an electronic system and a method for determining the fertility phase of a female human, which system and method rely on more than one indicative parameter, while being convenient and easy to use.

According to the present invention, these objects are achieved through the features of the independent claims. In addition, further advantageous embodiments follow from the dependent claims and the description.

According to the present invention, the above-mentioned objects are particularly achieved in that an electronic system for determining a fertility phase of a female human comprises a wearable device that includes a first sensor system, configured to be worn in contact with the skin of the female human and to determine heart rate and heart rate variability of the female human. The electronic system further comprises a processor that is configured to determine a change in pulse during a menstrual cycle, using the heart rate, and to determine the fertility phase, using the time of the change in the pulse.

In an embodiment, the electronic system further comprises a second sensor system, configured to determine acceleration of the female human. The processor is configured to detect, during menstrual cycles, sleep phases with resting pulse, using the heart rate variability and the acceleration. The processor is further configured to determine a change in the resting pulse during a menstrual cycle, using the heart rate, and to determine the fertility phase, using the time of the change in the resting pulse.

In an embodiment, the processor is configured to determine a predicted starting point of the fertility phase using the time of the change of the pulse (or resting pulse, respectively) from a comparatively short interval between heart beats to a comparatively longer interval between heart beats.

In an embodiment, the processor is configured to determine a predicted starting point of the fertility phase by detecting a time indicative of an end point of a period of pulses with a comparatively long interval between heart beats.

In a further embodiment, the predicted starting point of the fertility phase is determined from a combination, e.g. an average, of the values determined based on the time of the change of the pulse, from a comparatively short interval between heart beats to a comparatively longer interval between heart beats, and the detected time indicative of an end point of a period of pulses with a comparatively long interval between heart beats.

In an embodiment, the processor is configured to determine an end point of the fertility phase using the time of the change of the pulse (or resting pulse, respectively) from a comparatively long interval between heart beats to a comparatively shorter interval between heart beats.

In an embodiment, the electronic system further comprises a data store. The processor is further configured to store the heart rate in the data store and to determine the change in the pulse (or resting pulse, respectively) during a menstrual cycle by analyzing the heart rates stored during one or more menstrual cycles. For example, analyzing the heart rates includes comparing intervals between heart beats to defined threshold values.

In another embodiment, the electronic system further comprises a data store and the processor is further configured to store the heart rate variability and the acceleration in the data store. The processor is further configured to determine the sleep phases with resting pulse by analyzing the heart rate variability and the acceleration stored during a plurality of menstrual cycles.

In a further embodiment, the electronic system comprises a temperature sensor system configured to measure a wrist temperature of the female human. The processor is configured to determine a change in temperature during a menstrual cycle using the wrist temperature, and to determine the fertility phase using the time of the change in the temperature.

In an embodiment, the electronic system comprises a galvanic skin response sensor system configured to measure electrical resistance. The processor is configured to determine a change in the galvanic skin response during one or more menstrual cycles using the electrical resistance, and to determine the fertility phase using the time of the change in the galvanic skin response.

In yet another embodiment, the first sensor system is further configured to determine perfusion, and the processor is configured to determine a change in the perfusion during one or more menstrual cycles, and to determine the fertility phase using a time of the change in the perfusion.

In another embodiment, the processor is further configured to detect during menstrual cycles sleep phases, using the heart rate variability and the acceleration, to determine changes in timing of the sleep phases during one or more menstrual cycles, and to determine the fertility phase using changes in timing of the sleep phases.

In an embodiment, the processor is arranged in the wearable device and the processor is configured to determine the fertility phase using physiological parameters measured by the sensor systems of the wearable device.

In another embodiment, the processor comprises a processor arranged in an external system, separated from the wearable device. In different embodiments or configurations, the external system is a cloud-based computer system or a mobile communication device, e.g. a cellular phone. The wearable device further comprises a communication module configured to transmit physiological parameters measured by the sensor systems of the wearable device to the external system. The processor is configured to determine the fertility phase using the physiological parameters received from the wearable device.

In an embodiment, the processor comprises a first processor arranged in the wearable device and configured to determine the fertility phase using physiological parameters measured and stored in the wearable device. The processor comprises a second processor arranged in an external system, separated from the wearable device. The wearable device further comprises a communication module configured to transmit physiological parameters measured by the sensor systems of the wearable device to the external system. The second processor is configured to determine the fertility phase using the physiological parameters received from the wearable device. The possibility of having a processor in the (e.g. wrist worn) device and in an external system determine the fertility phase makes it possible to inform the user in off-line and on-line mode, depending on whether the external system, e.g. a cloud-based computer system, is accessible or not, whereby the external calculation is typically more accurate, because of a larger amount of historical data that is available and can be included in the determination.

In addition to the electronic system, the present invention also relates to a method of determining a fertility phase of a female human. The method comprises receiving in a processor from a first sensor system of a wearable device, worn in contact with the skin of the female human, heart rate and heart rate variability of the female human. The method further comprises the processor determining a change in pulse during a menstrual cycle of the female human using the heart rate, and the processor determining the fertility phase using a time of the change in the pulse.

In an embodiment, the method further comprises receiving in the processor from a second sensor system of the wearable device acceleration of the female human. The method further comprises detecting by the processor during menstrual cycles of the female human sleep phases with resting pulse, using the heart rate variability and the acceleration. The method further comprises the processor determining a change in the resting pulse during a menstrual cycle of the female human using the heart rate, and the processor determining the fertility phase using a time of the change in the resting pulse.

In an embodiment, the method further comprises storing the heart rate variability and the acceleration in a data store, and determining the sleep phases with resting pulse by analyzing the heart rate variability and the acceleration stored during a plurality of menstrual cycles.

In another embodiment, the method further comprises storing the heart rate in the data store, and determining the change in the pulse (or resting pulse, respectively) during a menstrual cycle by analyzing the heart rates stored during one or more menstrual cycles.

In an embodiment, the method comprises receiving further physiological parameters from sensor systems of the wearable device. The further physiological parameters include a temperature of the female human measured by a temperature sensor system, a galvanic skin response measured by an electrical resistance sensor system, and/or perfusion measured by the first sensor system. The method comprises determining a change in the further physiological parameters during a menstrual cycle, and determining the fertility phase using the time of the change in the further physiological parameters.

In an embodiment, the method comprises a processor arranged in the wearable device receiving physiological parameters from sensor systems of the wearable device. The processor stores the physiological parameters in a data store of the wearable device, and the processor determines the fertility phase using the physiological parameters stored in the data store of the wearable device.

In another embodiment, the method comprises a processor arranged in an external system, separated from the wearable device, receiving physiological parameters via a network from sensor systems of the wearable device. The processor stores the physiological parameters in a data store of the external system. The processor determines the fertility phase using the physiological parameters stored in the data store of the cloud-based computer system.

In addition to an electronic system and a method of determining a fertility phase of a female human, the present invention also relates to a computer program product comprising a non-transient computer-readable medium having stored thereon computer program code configured to control one or more processors of a computerized system. The computer program code is configured to control the one or more processors such that the computerized system: receives from a first sensor system of a wearable device, worn in contact with the skin of the female human, heart rate and heart rate variability of a female human, receives from a second sensor system of the wearable device acceleration of the female human, detects during menstrual cycles of the female human sleep phases with resting pulse using the heart rate variability and the acceleration, determines a change in the resting pulse during a menstrual cycle of the female human using the heart rate, and determines the fertility phase using a time of the change in the resting pulse.

In an embodiment, the computer program code is configured to control the one or more processors such that the computerized system receives from a second sensor system of the wearable device acceleration of the female human, detects during menstrual cycles of the female human sleep phases with resting pulse using the heart rate variability and the acceleration, determines a change in the resting pulse during a menstrual cycle of the female human using the heart rate, and determines the fertility phase using a time of the change in the resting pulse.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
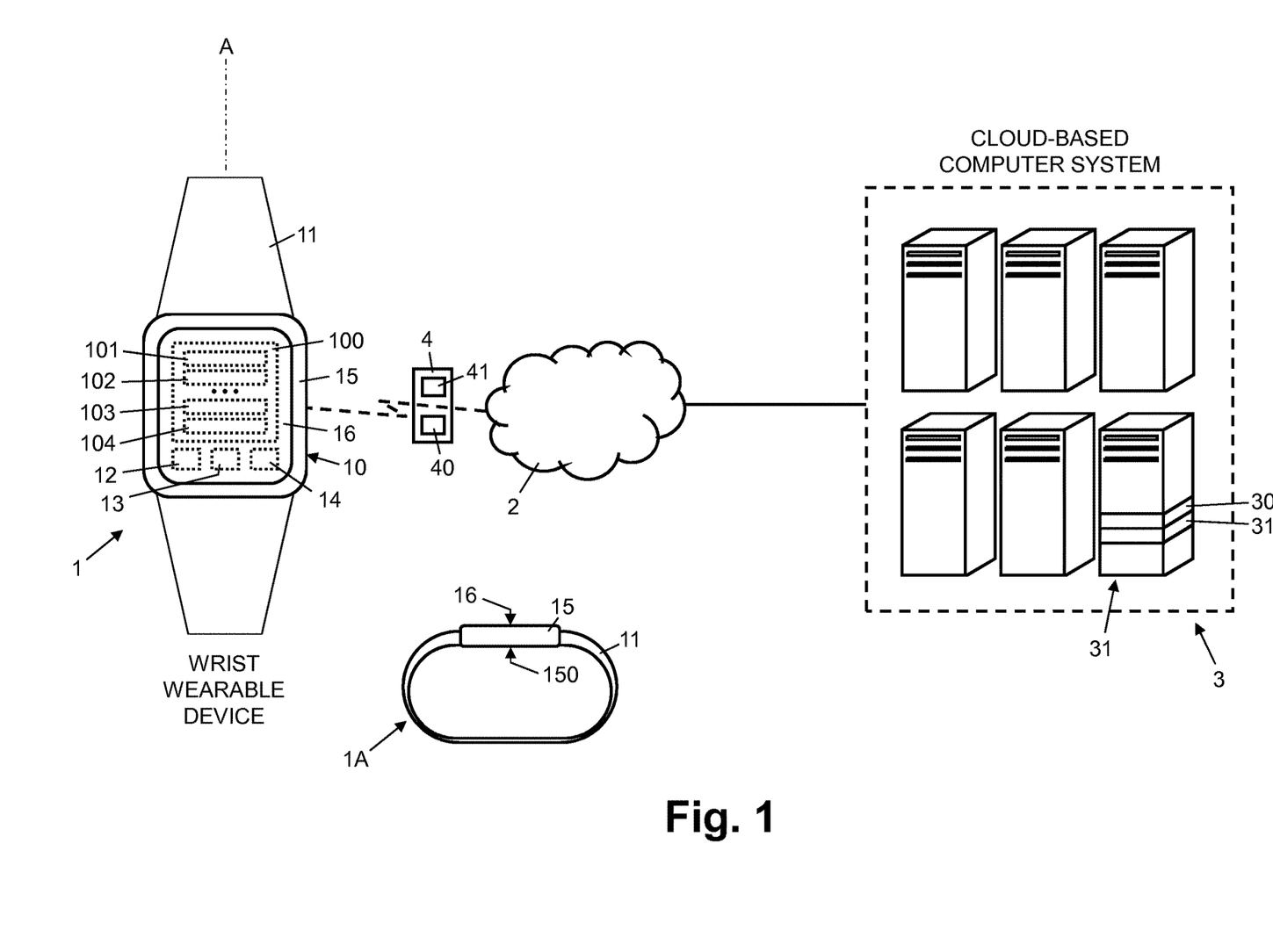
FIG. 1: shows a block diagram illustrating schematically an electronic system for determining a fertility phase of a female human, the system comprising a wearable device and a processor with a processor in the wearable device and/or an external system.

In FIG. 1, reference numeral 3 refers to a computer system, e.g. a cloud-based computer system, comprising one or more computers 31 with one or more processors 30 and a data storage system 31. The computer system 3 or its processors 30, respectively, are connected to the data storage system 31 and configured to execute various functions, as will be explained later in more detail. The data storage system 31 comprises RAM, flash memory, hard disks, data memory, and/or other data stores.

In FIG. 1, reference numeral 4 refers to a mobile communication device, e.g. a cellular telephone, comprising one or more processors 40 and a data store 41. The processors 40 are connected to the data store and configured to execute various functions, as will be explained later in more detail. The data store comprises RAM, flash memory, data memory, and/or other data storage systems.

In FIG. 1, reference numeral 1 refers to a wearable device, e.g. a wrist wearable device, specifically a wrist wearable electronic device. Reference numeral 1A refers to a cross-sectional view of the wearable device 1 along central axis A. The wearable device 1 includes a fixation system for attaching the wearable device 1 on the body of a user, specifically, for attaching the wearable device 1 in contact with the skin of the user; in the embodiment shown in FIG. 1, the wearable device 1 comprises a wrist band 11 and a device body 10 attached to or integrated in the wrist band 11. The wrist band 11 is implemented as a watch strap, a watch band, a bracelet, or the like. The device body 10 comprises a housing 15 and an optional display 16 integrated in the housing 15. As illustrated schematically in FIG. 1, wearable device 1 comprises several sensor systems 100, including a sensor system 101 with optical sensors 101 configured to generate photoplethysmography (PPG) signals for measuring heart rate, heart rate variability, and perfusion. For example, sensor system 101 comprises a PPG-based sensor system for measuring heart rate and heart rate variability as described in Simon Arberet et al., "Photoplethysmography-Based Ambulatory Heartbeat Monitoring Embedded into a Dedicated Bracelet", Computing in Cardiology 2013; 40:935-938, included herewith by reference in its entirety. The sensor systems 100 further include a sensor system 102 with one or more accelerometers for measuring body movements (acceleration). In an embodiment, for the purpose of sleep phase analysis the accelerometers are implemented in combination with the PPG-based sensor system, as described in Philippe Renevey et al., "PHOTOPLETHYSMOGRAPHY-BASED BRACELET FOR AUTOMATIC SLEEP STAGES CLASSIFICATION: PRELIMINARY RESULTS", IASTED 2014, Zurich, Switzerland, included herewith by reference in its entirety. Depending on the embodiment, the sensor systems 100 further include a galvanic skin response sensor system 103 with an electrical resistance or conductance measuring system, and/or a temperature sensor system 104 for measuring the user's temperature; specifically, the user's skin temperature; more specifically, the wrist's skin temperature. The temperature sensor system 104 comprises one or more sensors, including at least one temperature sensor. The optical sensors 101, the galvanic skin response sensor system 103, and the temperature sensor system 104 are integrated in the housing 15 of the wearable device 1 and are arranged on a rear side 150 of the wearable device 1, e.g. opposite of the optional display 16, facing the user's skin in a mounted state of the wearable device 1. In the mounted state when the device 1 is actually attached and worn, e.g. on the wrist, just as one would wear a watch, the rear side 150 of the wearable device 1 or the rear side 150 of its housing 15, respectively, is in contact with the skin, e.g. the skin of the wrist, i.e. the optical sensors 101, the galvanic skin response sensor system 103, and the temperature sensor system 104 touch the skin or at least face the skin, e.g. the skin of the wrist. The wearable device 1 further comprises a data store 12, e.g. data memory such as RAM or flush memory, and an operational processor 13 connected to the data store 12 and the sensor systems 100. The processor 13 comprises an electronic circuit configured to perform various functions that will be described later in more detail.

As illustrated in FIG. 1, in an embodiment, the wearable device 1 further comprises a communication module 14 connected to the processor 13. The communication module 14 is configured for data communication with an external system 3, 4, that is separated from the wearable device 1, i.e. a computerized system that is arranged in a different housing than the wearable device 1. Depending on the embodiment and/or configuration, the external system is a remote computer system 3 or a mobile communication device 4. Accordingly, the communication module 14 is configured for data communication with the remote computer system 3 via a network 2 and/or with the mobile communication device 4 via a close range communication interface. The network 2 comprises a mobile radio network such as a GSM-network (Global System for Mobile communication), a UMTS-network (Universal Mobile Telephone System), or another mobile radio telephone system, a wireless local area network (WLAN), and/or the Internet. For example, for close range communication, the communication module 14 comprises a Bluetooth communication module, e.g. a Low Energy Bluetooth module, or another close range communication module configured for direct data communication with the external mobile communication device 4. In an alternative embodiment, the mobile communication device 4 is configured to facilitate the data communication between the wearable device 1 and the remote computer system 3, e.g. by relaying the measurement data from the wearable device 1 via the network 2 to the remote computer system 3, for processing. Although not illustrated, the wearable device 1 further comprises a timer module configured to generate current time and date information, e.g. a clock circuit or a programmed timer module. The timer module is further configured to generate time stamps including the current time and date.

In the following examples, the functions executed by the processor 13 of the wearable device 1 and/or the processor(s) 30, 40 of the computer system 3 and/or the mobile communication device 4 are described with reference to FIGS. 2-6. Specifically, described are the functions executed by these processors 13, 30, 40 for determining and predicting a fertility phase of a female human.

Figure 2:
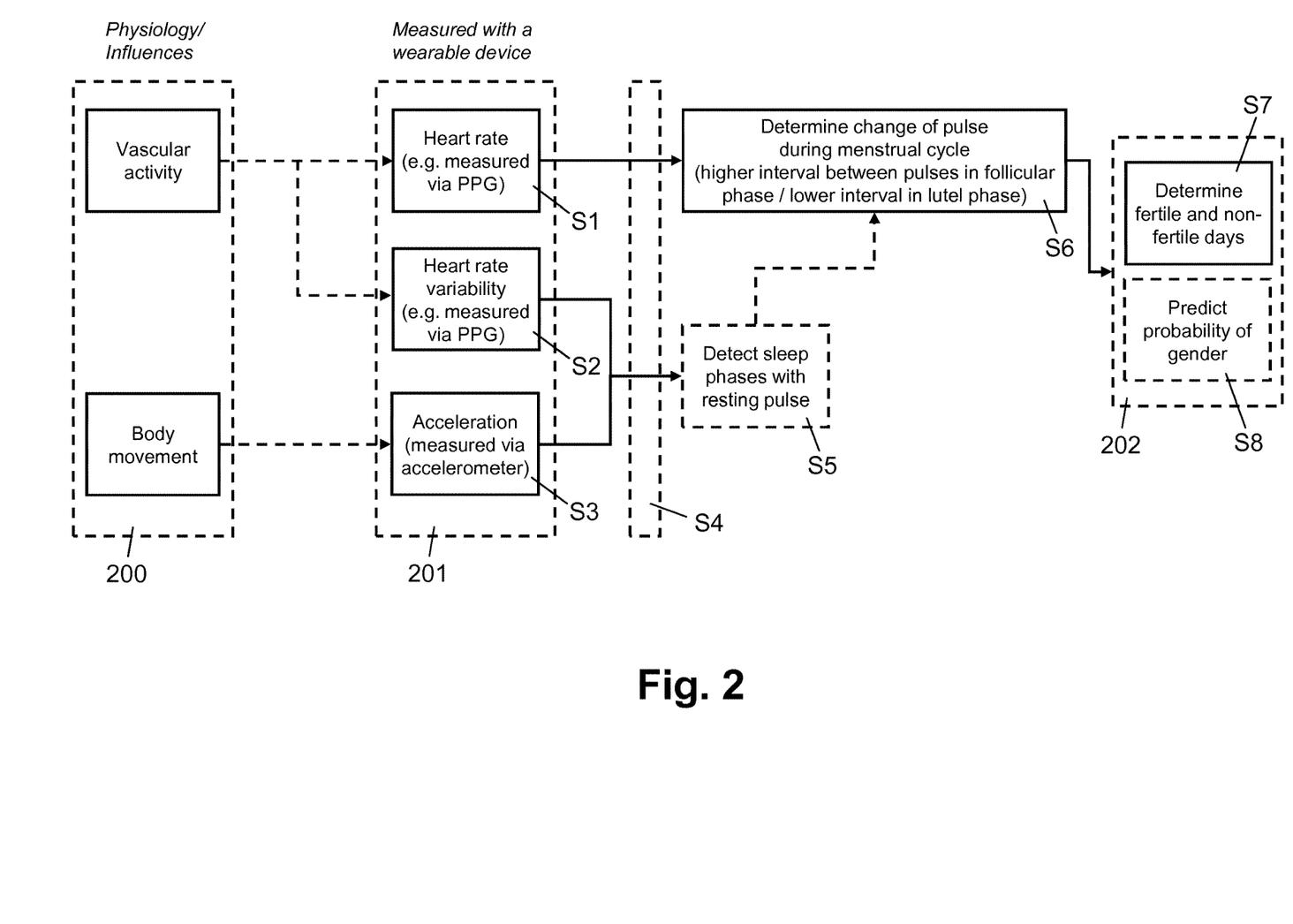
FIG. 2: shows a flow diagram illustrating schematically an exemplary sequence of steps for determining a fertility phase of a female human by analyzing the resting pulse during the menstrual cycle.

In FIG. 2, box 200 relates to physiological parameters and other physical influence factors, including vascular activity and body movement of the female user, which are taken into consideration for determining and predicting the fertility phase.

In FIG. 2, box 201 includes the actual physiological parameters and other indicators that are actually measured for determining and predicting the fertility phase.

As illustrated in FIG. 2, in step S1, the heart rate of the female user is measured using the wearable device 1. Specifically, in the state of the device 1 being worn, e.g. on the wrist, the processor 13 of the wearable device 1 reads or receives from the sensor system 101 the current heart rate of the female user. The processor 13 stores the heart rate (value) in the data store 12 together with a time stamp, including the current time and date.

In step S2, the heart rate variability of the female user is measured using the wearable device 1. Specifically, in the state of the device 1 being worn, e.g. on the wrist, the processor 13 of the wearable device 1 reads or receives from the sensor system 101 the current heart rate variability of the female user. The processor 13 stores the heart rate variability (value) in the data store 12 together with a time stamp, including the current time and date.

In step S3, the movement or acceleration, respectively, of the female user is measured using the wearable device 1. Specifically, in the state of the device 1 being worn, e.g. on the wrist, the processor 13 of the wearable device 1 reads or receives from the sensor system 102 the current acceleration of the female user, e.g. the current acceleration of her wrist. The processor 13 stores the acceleration (value) in the data store 12 together with a time stamp, including the current time and date. As will be explained later, in some simplified embodiments, step S3 is omitted, as the fertility phase is determined without using user acceleration.

Preferably, the measurements of the heart rate, heart rate variability, and acceleration of the female user are performed concurrently. The measurements are performed periodically, for example the sensor system 101 uses the optical sensors to measure the heart rate and heart rate variability every couple of milliseconds. In an embodiment, the periodic measurements are limited to specific time intervals, e.g. during night time.

Depending on the embodiment and/or configuration, further processing of the measured heart rate, heart rate variability, and acceleration of the female user is performed by the processor 13 of the wearable device and/or by the processor(s) 30, 40 of the computer system 3 and/or the mobile communication device 4. In the case, involving processing by the processor(s) 30 of the computer system 3, the measured and time stamped values of the heart rate, heart rate variability, and acceleration are transmitted by the communication module 14 from the wearable device 1 via network 2 to the computer system 3, as indicated by step S4 in FIG. 2, e.g. directly or via the mobile communication device 4 as a relay device. In the case, involving processing by the processor 40 of the mobile communication device 4, the measured and time stamped values of the heart rate, heart rate variability, and acceleration are transmitted by the communication module 14 from the wearable device 1 via the close range communication interface to the mobile communication device 4 where they are stored in the data store 41. In the computer system 3 and/or the mobile communication device 4, respectively, the received measurement values are stored securely assigned to the female user, defined, for example, by a user identifier and/or a device identifier (for increased anonymity/privacy). Transmission of the time stamped measurements is performed periodically, for example; typically, the measurement data is transmitted less frequently than the measurements are taken, e.g. various time stamped measurement samples, taken at different times, are grouped and transmitted together by the wearable device 1 in a combined data transmission.

In step S5, the heart rate variability and the acceleration are used (by the processor 13 of the wearable device and/or by the processor(s) 30, 40 of the computer system 3 and/or the mobile communication device 4) to detect sleep phases with a resting pulse. Detecting sleep phases with resting pulse makes it possible to detect the pulse each night during the menstrual cycle in the same state of activity and arousal of the female user. The sleep phases are detected, for example, by combining the measurements of the heart rate variability and acceleration as described by Renevey et al. cited above. In a simplified embodiment, the sleep phase is determined without using user acceleration, for example based on a user-defined sleep interval, e.g. between 3:00 am and 4:00 am.

In step S6, the processor 13 of the wearable device and/or the processor(s) 30, 40 of the computer system 3 and/or the mobile communication device 4 detect changes of the pulse, e.g. the resting pulse, during the menstrual cycle of the female user. In other words, the processor(s) 13, 30, 40 determine changes of the heart rate, i.e. changes in the duration of the interval between individual heart beats, respectively, that occur during the detected sleep phases with resting pulse. Specifically, the processor(s) 13, 30, 40 determine the points in time when the resting pulse changes from short to long intervals in the follicular phase 400 and when the resting pulse changes from long to short intervals in the luteal phase 401. Typically, the changes in the duration of the beat to beat intervals vary between 35 ms and 105 ms. For example, the NREM (Non-Rapid Eye Movement) phase is considered a sleep phases with resting pulse. In a simplified embodiment, the wearable device and/or the processor(s) 30, 40 of the computer system 3 and/or the mobile communication device 4 detect changes of the pulse during the menstrual cycle of the female, without a limitation to a detected sleep phase, but at a specific point in time, e.g. during the night, for example based on a user-defined sleep interval, e.g. between 3:00 am and 4:00 am.

Figure 4:
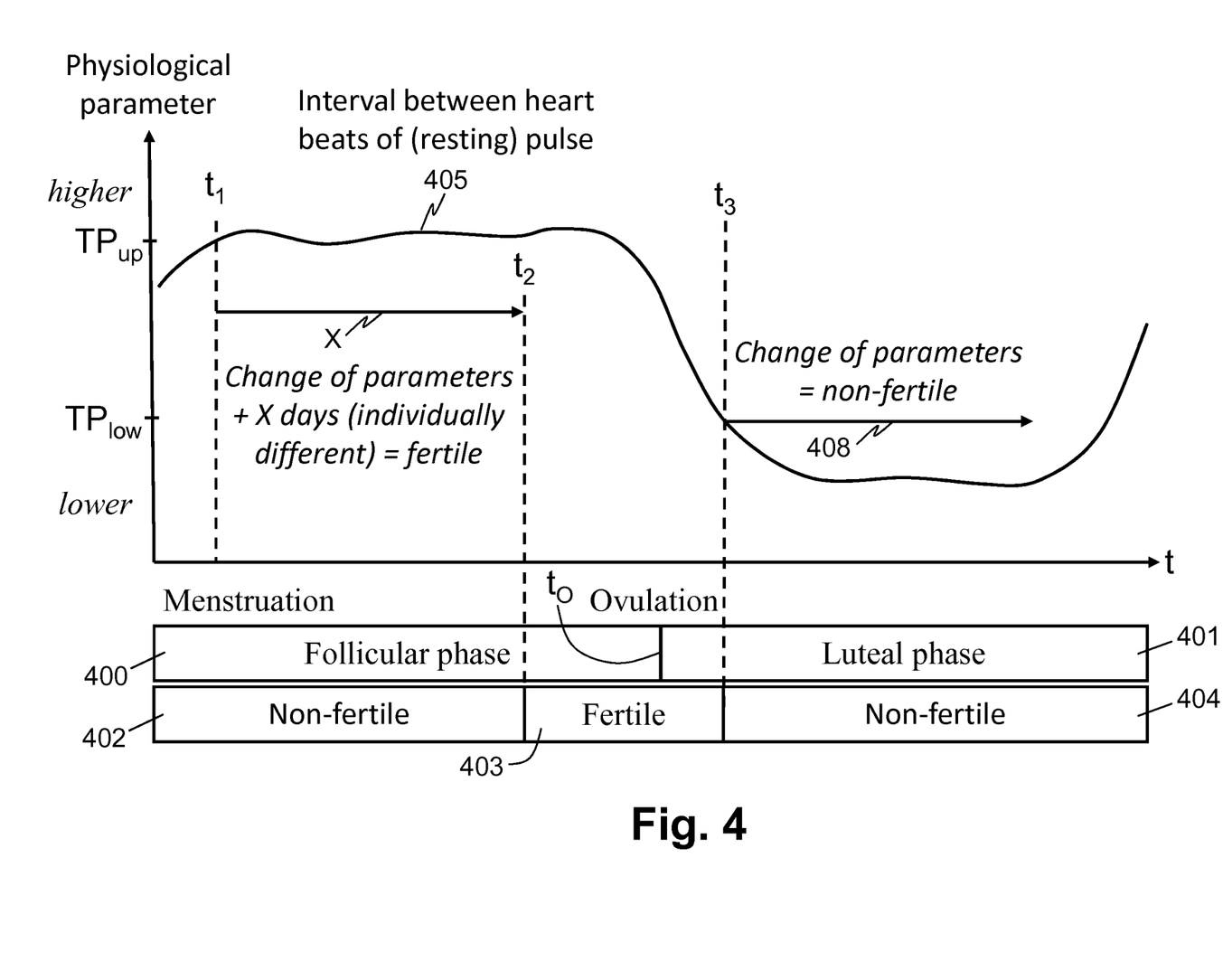
FIG. 4: shows a graph illustrating an example of the temporal change of the interval between heart beats of the resting pulse.
Figure 5:
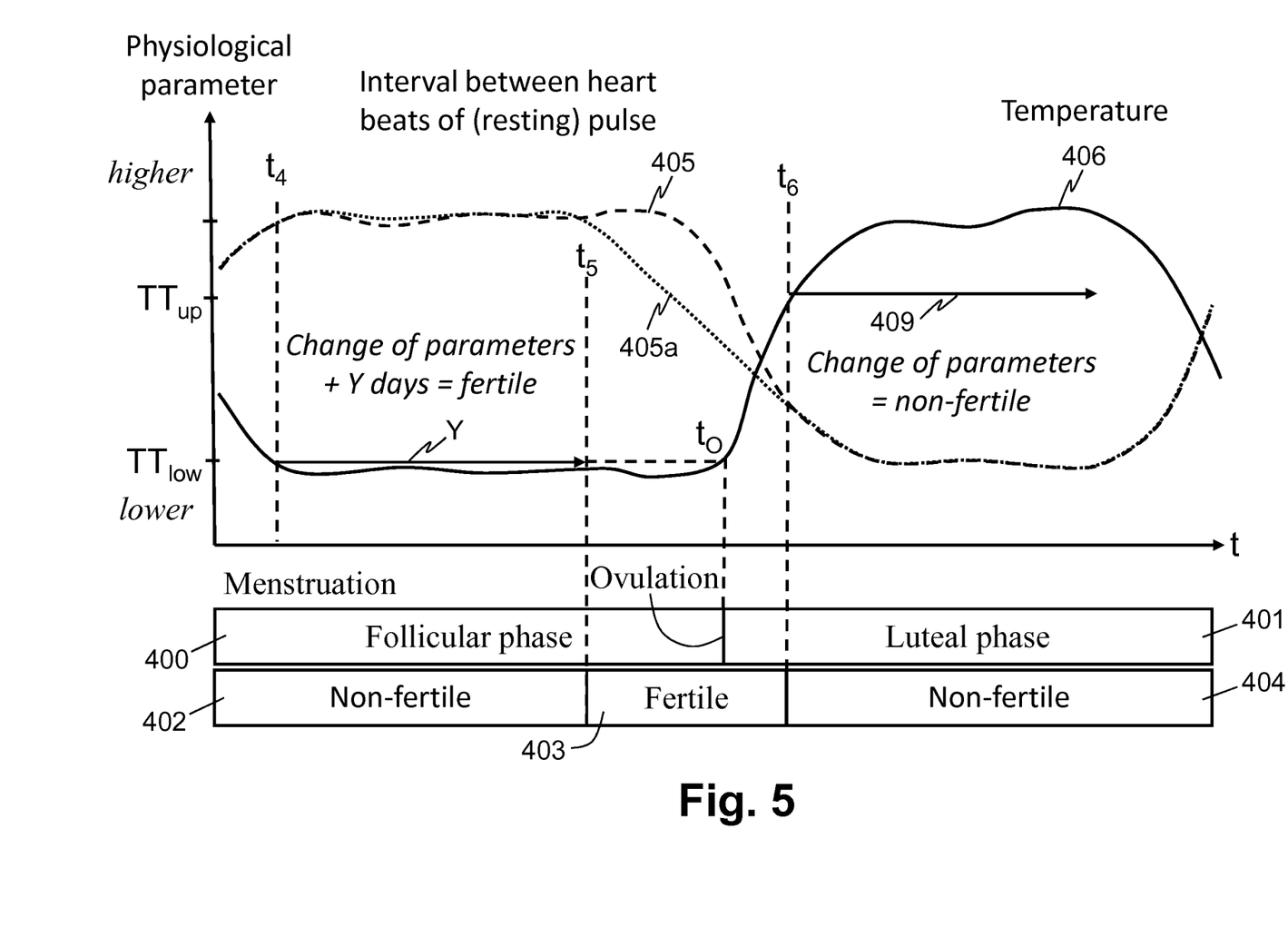
FIG. 5: shows a graph illustrating an example of the temporal change of temperature during the menstrual cycle as well as of the interval between heart beats of the resting pulse.
Figure 6:
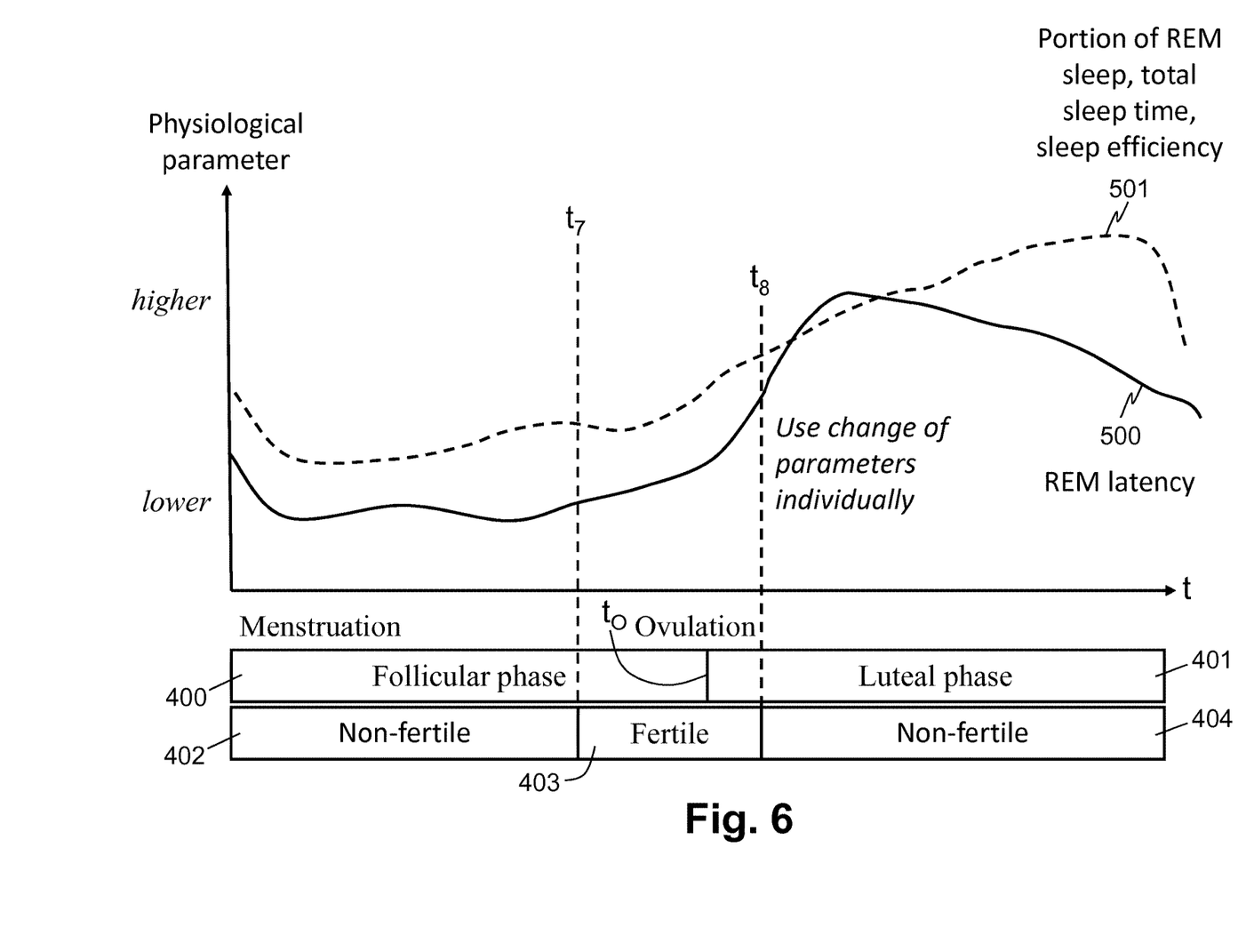
FIG. 6: shows a graph illustrating an example of the temporal change of sleep related parameters during the menstrual cycle.

As illustrated in FIGS. 4, 5, and 6, the menstrual cycle of a female human includes a follicular phase 400 and a luteal phase 401 which are separated by the time of ovulation $t_O$. As is further illustrated in FIGS. 4, 5, and 6, the fertile phase 403 of the female human begins before and ends after the time of ovulation $t_O$. The beginning of the follicular phase 400 is a non-fertile phase 402; the end of the luteal phase 401 is a non-fertile phase 404.

In FIG. 4, reference numeral 405 refers to the graph that shows the change of the interval between heart beats during the menstrual cycle. As is shown in the example of FIG. 4, in the follicular phase 400, the duration of the interval between heart beats is longer than the duration of the intervals between pulses in the luteal phase 401. The change of the resting pulse (from short to long intervals) in the follicular phase 400 is indicated by time $t_1$ when the duration of the interval between individual pulses exceeds a defined upper threshold $TP_{up}$. The change of the resting pulse (from long to short intervals) in the luteal phase 401 is indicated by time $t_3$ when the duration of the interval between individual pulses is below a defined lower threshold $TP_{low}$. The values of the upper and lower thresholds $TP_{up}$ and $TP_{low}$ are determined individually for the female user by the processor 13 of the wearable device and/or the processor(s) 30 of the computer system 3. The values of the upper and lower thresholds $TP_{up}$ and $TP_{low}$ are determined as a defined percentage p, q (for example p>90%, e.g. p=97%; q<110%, e.g. q=102%) of the maximum $PI_{max}$ and minimum levels $PI_{min}$ of the intervals between the heart beats recorded on average for the particular female users during a plurality n of menstrual cycles $$TP_{up} = p \cdot \left(\frac{1}{n}\sum_n PI_{max_n}\right) \text{ and}$$

$$TP_{low} = q \cdot \left(\frac{1}{n}\sum_n PI_{min_n}\right),$$

respectively.

In FIG. 2, block 202 refers to processing steps performed, by the processor 13 of the wearable device and/or the processor(s) 30, 40 of the computer system 3 and/or the mobile communication device 4, using the detected changes of the resting pulse.

In step S7, the processor(s) 13, 30, 40 calculate the fertile (and non-fertile) phases in the menstrual cycle of the female user based on the detected changes of the resting pulse. As illustrated in FIG. 4, the starting time $t_2$ of the fertile phase 403 is calculated, based on the point in time $t_1$ when the duration of the interval between individual pulses exceeds a defined upper threshold $TP_{up}$, by adding a defined user-specific time duration X to that time of change: $t_2=t_1+X$.

Figure 4A:
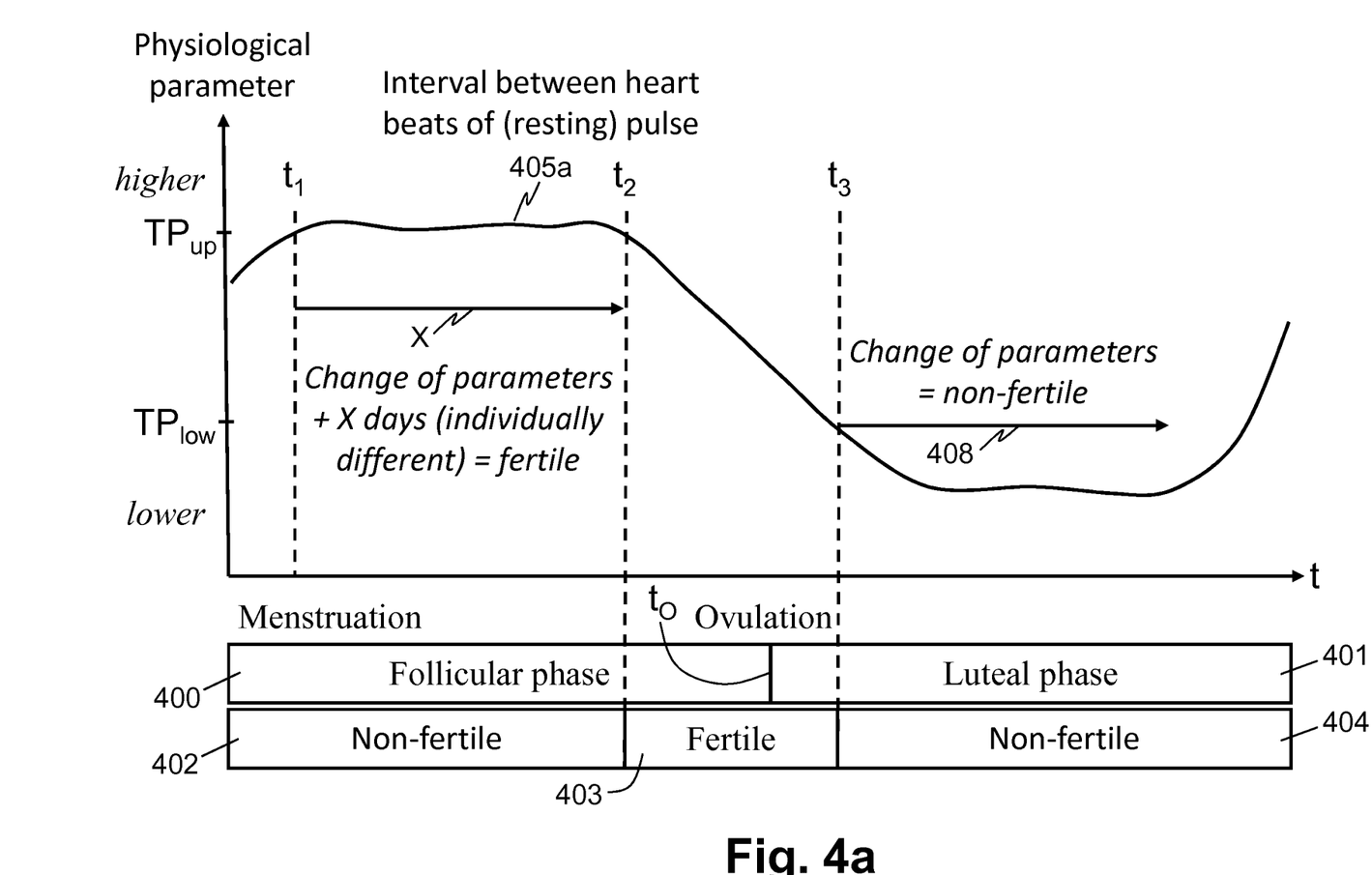
FIG. 4a: shows a graph illustrating another example of the temporal change of the interval between heart beats of the resting pulse.

In an embodiment, with individuals who show a course of the change of the interval between heart beats during the menstrual cycle as illustrated in FIGS. 4a and 5, and denoted by reference numeral 405a, the starting time $t_2$ of the fertile phase 403 can be determined, based on a detected end point of the period of pulses with the comparatively long interval between heart beats, e.g. at the point in time $t_2$ when the duration of the interval between individual pulses falls again below the defined upper threshold $TP_{up}$ or another defined threshold value. This end-point-based ($t_2$) approach can be executed as an alternative to the starting-time-based ($t_1+X$) approach for calculating the starting time $t_2$ of the fertile phase 403, or in combination with the starting-time-based ($t_1+X$), e.g. by calculating an average value from the results of the two approaches.

As further illustrated in FIG. 5, the ending time $t_3$ of the fertile phase 403 is defined based on the point in time $t_3$ when the duration of the interval between individual pulses is below the defined lower threshold $TP_{low}$.

For example, the user-specific time duration X is calculated as a defined percentage r (for example 50%≤r≤70%, e.g. r=60%) of the duration between the point in time $t_1$ when the duration of the interval between individual pulses exceeds the defined upper threshold $TP_{up}$ and the point in time $t_3$ when the duration of the interval between individual pulses is below a defined lower threshold $TP_{low}$, determined on average for the particular female user during a plurality n of menstrual cycles $$X = r \cdot \left(\frac{1}{n}\sum_n (t_{3_n} - t_{1_n})\right).$$

As will be described later, in further embodiments, additional physiological parameters and indicators are used to refine the timing of the fertility phase or the user-specific time duration X, respectively.

The user-specific fertile phase 403 [$t_2$,$t_3$] is shown to the user on the display 16 of the wearable device 1 or the mobile communication device 4 by the processor 13 or 40, respectively, e.g. as graphical representation including date and time of starting and end points $t_2$, $t_3$. Depending on the embodiment, the user-specific fertile phase 403 is transmitted by the processor(s) 30 of the computer system 3 via network 2 to the wearable device 1 and/or the mobile communication device 4.

Figure 3:
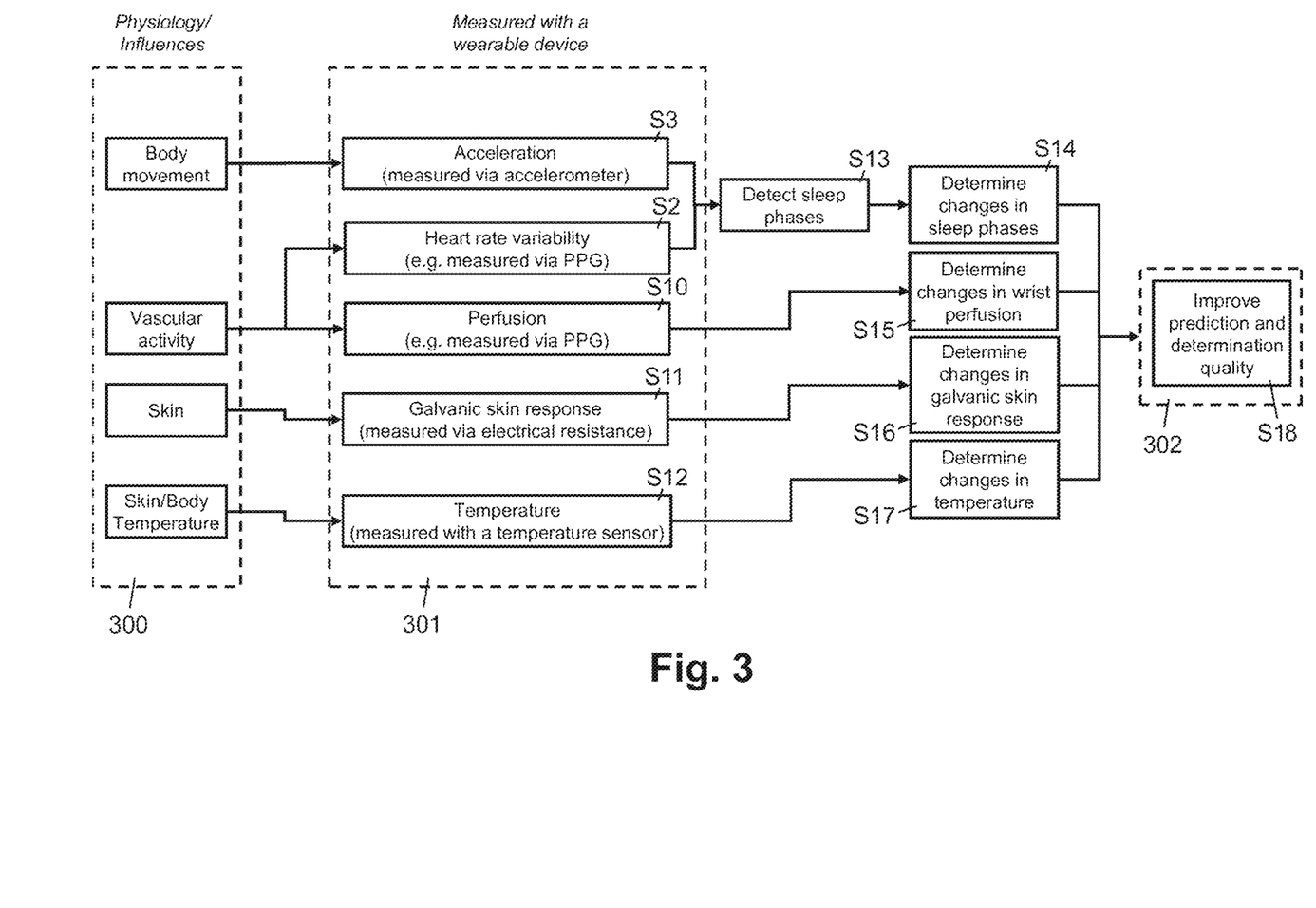
FIG. 3: shows a flow diagram illustrating schematically an exemplary sequence of steps for improving the prediction and determination of a fertility phase of a female human by analyzing further physiological parameters during the menstrual cycle.

In FIG. 3, box 300 relates to an extended set of physiological parameters and other physical influence factors, which are taken into consideration for determining and predicting the fertility phase, including—in addition to the vascular activity and body movement of the female user—skin and body temperature.

In FIG. 3, box 301 includes an extended set of the actual physiological parameters and other indicators that are actually measured for determining and predicting the fertility phase.

As illustrated in FIG. 3, in step S10, the perfusion of the female user, e.g. the wrist perfusion, is measured using the wearable device 1. Specifically, in the state of the device 1 being worn, e.g. on the wrist, the processor 13 of the wearable device 1 reads or receives from the sensor system 101 the current (wrist) perfusion of the female user. The processor 13 stores the perfusion (value) in the data store 12 together with a time stamp, including the current time and date.

In step S11, the galvanic skin response of the female user's, e.g. on her wrist, is measured using the wearable device 1. Specifically, in the state of the device 1 being worn, e.g. on the wrist, the processor 13 of the wearable device 1 reads or receives from the galvanic skin response sensor system 103 the current electrical resistance or conductance of the skin of the female user's, e.g. of the wrist. The processor 13 stores the galvanic skin response (value) in the data store 12 together with a time stamp, including the current time and date.

In step S12, the wrist temperature of the female user is measured using the wearable device 1. Specifically, in the state of the device 1 being worn, e.g. on the wrist, the processor 13 of the wearable device 1 reads or receives from the temperature sensor system 104 the currently measured temperature of the female user, specifically the skin temperature, e.g. on her wrist. The processor 13 stores the temperature (value) in the data store 12 together with a time stamp, including the current time and date.

Preferably, the measurements of the heart rate, heart rate variability, perfusion, acceleration, temperature, and galvanic skin response of the female user are performed concurrently. The measurements are performed periodically, e.g. once or more every second. In an embodiment, the periodic measurements are limited to specific time intervals, e.g. during night time.

As described above in the context of FIGS. 2 and 4, depending on the embodiment and/or configuration, further processing of the measured parameters and indicators is performed by the processor 13 of the wearable device and/or by the processor(s) 30 of the computer system 3. In the latter case, the measured and time stamped parameters and indicators are transmitted from the wearable device 1 via network 2 to the computer system 3 where they are stored securely assigned to the female user and/or her device, respectively.

In step S13, the heart rate variability and the acceleration are used by the processor(s) 13, 30 to detect different sleep phases, e.g. by combining the measurements of the heart rate variability and acceleration as described by Renevey et al. cited above.

In step S14, the processor(s) 13, 30 detect changes of the sleep phases during the menstrual cycle of the female user.

In step S15, the processor(s) 13, 30 detect changes of the perfusion during the menstrual cycle of the female user.

In step S16, the processor(s) 13, 30 detect changes of the galvanic skin response during the menstrual cycle of the female user.

In step S17, the processor(s) 13, 30 detect changes of the measured body or wrist temperature during the menstrual cycle of the female user. Typically, the changes vary between 0.24° C.-0.5° C.

It should be pointed out, that the changes of the resting pulse, the sleep phases, the perfusion, of the galvanic skin response, and the temperature are detected in steps S6, S14, S15, S16, and S17, respectively, for measurements recorded during the current menstrual cycle with respect to their dynamic (temporal) change in the course of the current menstrual cycle and/or with respect to measurements recorded for previous menstrual cycles of the female user. A specific dynamic change of a parameter is detected by comparing the measurements of the particular parameter to defined thresholds and identifying the change or its point in time, respectively, when the parameter exceeds or is below the particular threshold. A change of a parameter with regards to measurements recorded in previous menstrual cycles is detected by comparing the measurements of the particular parameter to thresholds that are defined depending on measurements recorded in previous menstrual cycles.

In FIG. 3, block 302 refers to processing steps performed by the processor(s) 13, 30 to improve accuracy and quality of determining the fertile phases of the female user based on the parameters and indicators determined in steps S2, S3, S10, S11, S12, and S13, and processed in steps S14, S15, S16, and S17.

In one embodiment, in step S18, the processor(s) 13, 30 use the detected temperature changes to improve accuracy and quality of pulse-based determination of the fertile phases of the female user.

In FIG. 5, reference numeral 406 refers to the graph that shows the course of the measured temperature during the menstrual cycle. As is shown in the example of FIG. 5, in the follicular phase 400, the temperature is lower than in the luteal phase 401. The change of temperature (from high to low) in the follicular phase 400 is indicated by time $t_4$ when the temperature is below a defined lower threshold $TT_{low}$. The change of the temperature (from low to high) in the luteal phase 401 is indicated by time $t_6$ when the temperature exceeds a defined upper threshold $TT_{up}$. The values of the upper and lower thresholds $TT_{up}$ and $TT_{low}$ are determined individually for the female user by the processor 13 of the wearable device and/or the processor(s) 30 of the computer system 3. Moreover, the time of ovulation $t_O$ is determined by the processor 13 of the wearable device and/or the processor(s) 30 of the computer system 3 as the time when the temperature exceeds the defined lower threshold $TT_{low}$. The values of the upper and lower thresholds $TT_{up}$ and $TT_{low}$ are determined as a defined percentage u, v (for example u>90%, e.g. u=97%; v<110%, e.g. v=102%) of the maximum temperature $T_{max}$ and minimum temperature levels $T_{min}$ of the temperature recorded on average for the particular female user, during a plurality n of menstrual cycles $$TT_{up} = u \cdot \left(\frac{1}{n}\sum_n T_{max_n}\right) \text{ and } TT_{low} = v \cdot \left(\frac{1}{n}\sum_n T_{min_n}\right),$$

respectively.

Accordingly, in step S18, the processor(s) 13, 30 further calculate the fertile (and non-fertile) phases in the menstrual cycle of the female user based on the determined temperature. As illustrated in FIG. 5, the starting time $t_5$ of the fertile phase 403 is calculated based on the point in time $t_4$, when the temperature is below the defined lower threshold $TT_{low}$, by adding a defined time duration Y to that time: $t_5=t_4+Y$. As further illustrated in FIG. 5, the ending time $t_6$ of the fertile phase 403 is defined based on the point in time $t_6$ when the temperature exceeds the defined upper threshold $TT_{up}$.

For example, the user-specific time duration Y is calculated as a defined percentage w (for example 55%≤w≤75%, e.g. w=65%) of the duration between the point in time $t_4$, when the temperature is below the defined lower threshold $TT_{low}$, and the point in time $t_6$, when the temperature exceeds the defined upper threshold $TT_{up}$, determined on average for the particular female user during a plurality n of menstrual cycles $$Y = w \cdot \left(\frac{1}{n}\sum_n (t_{4_n} - t_{6_n})\right).$$

Subsequently, the improved user-specific fertile phase 403 is calculated by taking into consideration the pulse-based and the temperature-based calculations, e.g. by weighted or non-weighted averaging of the respective time values resulting in a refined user-specific fertile phase 403

$$\left[\frac{t_2+t_5}{2}, \frac{t_3+t_6}{2}\right]$$

or $[\alpha t_2+\beta t_5, \gamma t_3+\delta t_6]$ with weighting factors α, β, γ, δ, respectively. The user-specific fertile phase 403 is shown to the user on the display 16 of the wearable device 1 or the mobile communication device 4 by the processor 13 or 40, respectively. Depending on the embodiment, the user-specific fertile phase 403 is transmitted by the processor(s) 30 of the computer system 3 via network 2 to the wearable device 1 and/or the mobile communication device 4.

In another embodiment, in step S18, the processor(s) 13, 30 use the detected changes in sleep phases to improve accuracy and quality of pulse-based determination of the fertile phases of the female user.

In FIG. 6, reference numeral 500 refers to a graph that shows the course of REM latency based on measurements according to Renevey, as described above. The graph denoted by reference numeral 501 is representative of the course of various characteristics or parameters of sleep, e.g. the portion of REM sleep, the total sleep time, indicators of sleep efficiency, etc. The points in time $t_7$ and $t_8$ define the beginning point and the end point of the fertile phase 403 as determined by the processor(s) 13, 30 based on changes in the REM latency 500 or other sleep characteristics 501 within the current menstrual cycle and/or with respect to the REM latency 500 or other sleep characteristics 501 recorded for previous menstrual cycles of the female user. As described in the context of temperature-based improvement, the improved user-specific fertile phase 403 is calculated by taking into consideration the pulse-based, the temperature-based, and/or the sleep-based calculations, e.g. by weighted or non-weighted averaging of the respective time values, resulting in a refined user-specific fertile phase 403

$$\left[\frac{t_2+t_5}{2}, \frac{t_3+t_6}{2}\right],$$

$$[\alpha t_2 \beta t_5, \gamma t_3 + \delta t_6],$$

$$\left[\frac{t_2+t_7}{2}, \frac{t_3+t_8}{2}\right],$$

$$[\varepsilon t_2 + \phi t_7, \varphi t_3 + \lambda t_8],$$

$$\left[\frac{t_2+t_5+t_7}{3}, \frac{t_3+t_6+t_8}{3}\right],$$

or $[\mu t_2+\nu t_5+o t_7, \pi t_3+\omega t_6+\theta t_8]$, with weighting factors $\alpha$, $\beta$, $\gamma$, $\delta$, $\varepsilon$, $\phi$, $\varphi$, $\lambda$, $\mu$, $\nu$, $o$, $\pi$, $\omega$, $\theta$, respectively.

In optional step S8 of FIG. 2, the processor(s) 13, 30 determine a probability of the gender of a child conceived during the time of insemination 403, using the current time t with respect to the determined fertile phase 403; particularly, with respect to the time of ovulation $t_O$. The currently determined probability for male and/or female gender is shown to the user on the display 16 of the wearable device 1 or the mobile communication device 4 by the processor 13 or 40, respectively. Depending on the embodiment, the currently determined gender is transmitted by the processor(s) 30 of the computer system 3 via network 2 to the wearable device 1 and/or the mobile communication device 4. In the early stage of the fertile phase the probability for conceiving a male child are higher (e.g. 65%), while at the later stage, the probability of conceiving a female child are higher (e.g. 55%), as described in R. Guerrero, "Association of the Type and Time of Insemination Within Menstrual Cycle with the Human Sex Ratio at Birth," The New England Journal, Nov. 14, 1974.

In an embodiment, the processors 30 of the cloud-based computer system 3 are configured to implement an online user platform. The online user platform is configured to provide to authorized users secured access to their private personal data and stored measurement data.

It should be noted that, in the description, the computer program code has been associated with specific functional modules and the sequence of the steps has been presented in a specific order, one skilled in the art will understand, however, that the computer program code may be structured differently and that the order of at least some of the steps could be altered, without deviating from the scope of the invention.

The invention claimed is:

1. An electronic system for determining a fertility phase of a female human, the system comprising:
   a wearable device including a first sensor system configured to be worn in contact with skin of the female human and to determine heart rate and heart rate variability of the female human; and
   a processor configured to:
      determine a change in pulse during a menstrual cycle using the heart rate, and to determine the fertility phase using a time of the change in the pulse, wherein the fertility phase has a predicted starting point and a predicted end point;
      determine the predicted starting point of the fertility phase using the time of the change of the pulse from a comparatively short interval between heart beats to a comparatively longer interval between heart beats;
      determine the predicted end point of the fertility phase using the time of the change of the pulse from a comparatively long interval between heart beats to a comparatively shorter interval between heart beats; and
      output the fertility phase on a display of the wearable device.

2. The electronic system of claim 1, wherein the electronic system further comprises a data store, the processor is further configured to store the heart rate in the data store, and to determine the change in the pulse during a menstrual cycle by analyzing the heart rates stored during one or more menstrual cycles.

3. The electronic system of claim 1, wherein the electronic system further comprises a second sensor system configured to determine acceleration of the female human; and the processor is configured to detect, during menstrual cycles, sleep phases with resting pulse using the heart rate variability and the acceleration, to determine a change in the resting pulse during a menstrual cycle using the heart rate, and to determine the fertility phase using a time of the change in the resting pulse.

4. The electronic system of claim 3, wherein the electronic system further comprises a data store, the processor is further configured to store the heart rate variability and the acceleration in the data store, and to determine the sleep phases with resting pulse by analyzing the heart rate variability and the acceleration stored during a plurality of menstrual cycles.

5. The electronic system of claim 1, wherein the electronic system comprises a temperature sensor system configured to measure a wrist temperature of the female human, and the processor is configured to determine a change in temperature during a menstrual cycle using the wrist temperature, and to determine the fertility phase using a time of the change in the temperature.

6. The electronic system of claim 1, wherein the electronic system comprises a galvanic skin response sensor system configured to measure electrical resistance, and the processor is configured to determine a change in galvanic skin response during one or more menstrual cycles using the electrical resistance, and to determine the fertility phase using a time of the change in the galvanic skin response.

7. The electronic system of claim 1, wherein the first sensor system is further configured to determine perfusion, and the processor is configured to determine a change in the perfusion during one or more menstrual cycles, and to determine the fertility phase using a time of the change in the perfusion.

8. The electronic system of claim 1, wherein the processor is further configured to detect during menstrual cycles sleep phases using the heart rate variability and acceleration, to determine changes in timing of the sleep phases during one or more menstrual cycles, and to determine the fertility phase using changes in timing of the sleep phases.

9. The electronic system of claim 1, wherein the processor is arranged in the wearable device and configured to determine the fertility phase using physiological parameters measured by the first sensor system of the wearable device.

10. The electronic system of claim 1, wherein the processor is arranged in an external system, separated from the wearable device, the wearable device further comprises a communication module configured to transmit physiological parameters measured by the first sensor system of the wearable device to the external system, and the processor is configured to determine the fertility phase using the physiological parameters received from the wearable device.

11. The electronic system of claim 1, wherein the electronic system comprises a first processor arranged in the wearable device and configured to determine the fertility phase using physiological parameters measured and stored in the wearable device, the electronic system comprises a second processor arranged in an external system, separated from the wearable device, the wearable device further comprises a communication module configured to transmit physiological parameters measured by the first sensor system of the wearable device to the external system, and the second processor is configured to determine the fertility phase using the physiological parameters received from the wearable device.

12. A method of determining a fertility phase of a female human, the method comprising:
receiving in a processor from a first sensor system of a wearable device, worn in contact with skin of the female human, heart rate and heart rate variability of the female human;
determining, by the processor, a change in pulse during a menstrual cycle of the female human using the heart rate;
determining, by the processor, the fertility phase using a time of the change in the pulse, wherein the fertility phase has a predicted starting point and a predicted end point;
determining the predicted starting point of the fertility phase using the time of the change of the pulse from a comparatively short interval between heart beats to a comparatively longer interval between heart beats;
determining the predicted end point of the fertility phase using the time of the change of the pulse from a comparatively long interval between heart beats to a comparatively shorter interval between heart beats; and
outputting the fertility phase on a display of the wearable device.

13. The method of claim 12, wherein the method further comprises receiving in the processor, from a second sensor system of the wearable device, acceleration of the female human; detecting, by the processor during menstrual cycles sleep phases of the female human sleep phases with resting pulse using the heart rate variability and the acceleration; determining by the processor a change in resting pulse during a menstrual cycle of the female human using the heart rate; and determining, by the processor, the fertility phase using a time of the change in the resting pulse.

14. The method of claim 13, wherein the method further comprises storing the heart rate variability and the acceleration in a data store; determining the sleep phases with resting pulse by analyzing the heart rate variability and the acceleration stored during a plurality of menstrual cycles; storing the heart rate in the data store; and determining the change in the resting pulse during a menstrual cycle by analyzing the heart rates stored during one or more menstrual cycles.

15. The method of claim 12, wherein the method comprises receiving further physiological parameters from sensor systems of the wearable device, the further physiological parameters including at least one of: temperature of the female human measured by a temperature sensor system, galvanic skin response measured by an electrical resistance sensor system, and perfusion measured by the first sensor system; determining a change in the further physiological parameters during a menstrual cycle; and determining the fertility phase using a time of the change in the further physiological parameters.

16. The method of claim 12, wherein the method comprises a processor arranged in the wearable device receiving physiological parameters from sensor systems of the wearable device; the processor storing the physiological parameters in a data store of the wearable device; and the processor determining the fertility phase using the physiological parameters stored in the data store of the wearable device.

17. The method of claim 12, wherein the method comprises a second processor arranged in an external system, separated from the wearable device, and the second processor receiving physiological parameters from the first sensor system of the wearable device; the second processor storing the physiological parameters in a data store of the external system; the second processor determining the fertility phase using the physiological parameters stored in the data store of the external system; and the second processor transmitting information about the fertility phase to the wearable device.

18. A computer program product comprising a non-transient computer readable medium having stored thereon computer executable program code configured to control one or more processors of a computerized system, such that the computerized system:
receives from a first sensor system of a wearable device, worn in contact with skin of a female human, heart rate and heart rate variability of a female human;
determines a change in pulse during a menstrual cycle of the female human using the heart rate;
determines a fertility phase, using a time of the change in the pulse, wherein the fertility phase has a predicted starting point and a predicted end point;
determines the predicted starting point of the fertility phase using the time of the change of the pulse from a comparatively short interval between heart beats to a comparatively longer interval between heart beats;
determines the predicted end point of the fertility phase using the time of the change of the pulse from a comparatively long interval between heart beats to a comparatively shorter interval between heart beats; and outputs the fertility phase on a display of the wearable device.

\* \* \* \* \*